(12) United States Patent
Godwin et al.

(10) Patent No.: US 11,944,272 B2
(45) Date of Patent: Apr. 2, 2024

(54) SYSTEM AND METHOD FOR ASSISTING VISUALIZATION DURING A PROCEDURE

(71) Applicant: Medtronic Xomed, Inc., Jacksonville, FL (US)

(72) Inventors: Kyle A. Godwin, Cameron Park, CA (US); James Britton Hissong, Jacksonville, FL (US); Christopher S. Kellar, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 187 days.

(21) Appl. No.: 16/210,647

(22) Filed: Dec. 5, 2018

(65) Prior Publication Data

US 2019/0175058 A1 Jun. 13, 2019

Related U.S. Application Data

(60) Provisional application No. 62/595,822, filed on Dec. 7, 2017.

(51) Int. Cl.
*A61B 34/20* (2016.01)
*A61B 1/04* (2006.01)
(Continued)

(52) U.S. Cl.
CPC ............ *A61B 1/04* (2013.01); *A61B 1/233* (2013.01); *A61B 5/0077* (2013.01); *A61B 5/064* (2013.01); *A61B 5/065* (2013.01); *A61B 5/066* (2013.01); *A61B 34/20* (2016.02); *A61B 90/37* (2016.02); *A61B 90/39* (2016.02); *G06T 7/73* (2017.01); *G06T 11/60* (2013.01); *H04N 7/181* (2013.01); *A61B 2034/2051* (2016.02); *A61B 2034/2055* (2016.02); *A61B 2034/2057* (2016.02); *A61B 2034/2065* (2016.02); *A61B 90/361* (2016.02); *A61B 2090/363* (2016.02); *A61B 2090/365* (2016.02); *A61B 2090/371* (2016.02);
(Continued)

(58) Field of Classification Search
CPC .......... A61B 34/20; A61B 5/065; A61B 90/37
USPC ......................................................... 600/424
See application file for complete search history.

(56) References Cited

U.S. PATENT DOCUMENTS

| | | |
|---|---|---|
| 4,395,731 A | 7/1983 | Schoolman |
| 6,901,941 B2 | 6/2005 | Gershtein et al. |

(Continued)

FOREIGN PATENT DOCUMENTS

| | | |
|---|---|---|
| CN | 103238339 A | 8/2013 |
| CN | 104939925 A | 9/2015 |

(Continued)

OTHER PUBLICATIONS

International Search Report and Written Opinion dated Feb. 22, 2019 in corresponding/related International Application No. PCT/US2018/064280.

(Continued)

*Primary Examiner* — Patricia J Park
(74) *Attorney, Agent, or Firm* — Harness, Dickey & Pierce, P.L.C.

(57) ABSTRACT

A system operable to allowing viewing of a physical subject with information regarding at least an item separate from the subject overlaid thereon. The system includes a viewscreen. The system is further able to determine the position of the item relative to the subject.

19 Claims, 7 Drawing Sheets

(51) Int. Cl.
*A61B 1/233* (2006.01)
*A61B 5/00* (2006.01)
*A61B 5/06* (2006.01)
*A61B 90/00* (2016.01)
*G06T 7/73* (2017.01)
*G06T 11/60* (2006.01)
*H04N 7/18* (2006.01)
*A61B 90/50* (2016.01)
*G02B 27/01* (2006.01)
*H04N 5/272* (2006.01)

(52) U.S. Cl.
CPC ... *A61B 2090/372* (2016.02); *A61B 2090/376* (2016.02); *A61B 2090/3762* (2016.02); *A61B 2090/3937* (2016.02); *A61B 2090/3954* (2016.02); *A61B 2090/3966* (2016.02); *A61B 2090/3983* (2016.02); *A61B 2090/3991* (2016.02); *A61B 2090/502* (2016.02); *G02B 2027/0132* (2013.01); *G02B 2027/0134* (2013.01); *G02B 2027/0138* (2013.01); *G02B 2027/014* (2013.01); *G02B 2027/0141* (2013.01); *G02B 27/0172* (2013.01); *G06T 2207/30204* (2013.01); *H04N 5/272* (2013.01)

(56) References Cited

U.S. PATENT DOCUMENTS

| | | | |
|---|---|---|---|
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 8,238,631 B2 | 8/2012 | Hartmann et al. | |
| 8,467,133 B2* | 6/2013 | Miller | G06F 3/005 |
| | | | 359/630 |
| 8,600,478 B2 | 12/2013 | Verard et al. | |
| 8,644,907 B2 | 2/2014 | Hartmann et al. | |
| 8,670,816 B2 | 3/2014 | Green et al. | |
| 8,842,893 B2 | 9/2014 | Teichman et al. | |
| 8,891,847 B2 | 11/2014 | Helm et al. | |
| 9,411,057 B2 | 8/2016 | Helm et al. | |
| 9,412,200 B2 | 8/2016 | Helm et al. | |
| 9,486,628 B2 | 11/2016 | Christopherson et al. | |
| 9,675,319 B1* | 6/2017 | Razzaque | A61B 6/032 |
| 9,807,860 B2 | 10/2017 | Helm et al. | |
| 9,889,299 B2 | 2/2018 | Ni et al. | |
| 10,639,104 B1 | 5/2020 | Barral et al. | |
| 2002/0075201 A1 | 6/2002 | Sauer et al. | |
| 2003/0117369 A1 | 6/2003 | Spitzer et al. | |
| 2003/0163038 A1 | 8/2003 | Simon et al. | |
| 2005/0085714 A1 | 4/2005 | Foley et al. | |
| 2005/0203367 A1 | 9/2005 | Ahmed et al. | |
| 2005/0228270 A1 | 10/2005 | Lloyd et al. | |
| 2005/0289472 A1* | 12/2005 | Morita | G06F 3/011 |
| | | | 715/757 |
| 2007/0184422 A1 | 8/2007 | Takahashi | |
| 2009/0068620 A1 | 3/2009 | Knobel et al. | |
| 2009/0088634 A1 | 4/2009 | Zhao et al. | |
| 2009/0088830 A1 | 4/2009 | Mohamed et al. | |
| 2009/0326318 A1 | 12/2009 | Tognaccini et al. | |
| 2010/0228117 A1 | 9/2010 | Hartmann | |
| 2010/0290690 A1 | 11/2010 | Hartmann et al. | |
| 2012/0097178 A1 | 4/2012 | Helm et al. | |
| 2012/0099768 A1 | 4/2012 | Helm et al. | |
| 2012/0099772 A1 | 4/2012 | Helm et al. | |
| 2012/0250818 A1 | 10/2012 | Helm et al. | |
| 2012/0250822 A1 | 10/2012 | Helm et al. | |
| 2013/0060146 A1 | 3/2013 | Yang et al. | |
| 2013/0072787 A1* | 3/2013 | Wallace | A61B 90/50 |
| | | | 600/424 |
| 2013/0188848 A1 | 7/2013 | Helm et al. | |
| 2013/0237811 A1 | 9/2013 | Mihailescu et al. | |
| 2013/0267833 A1 | 10/2013 | Schroeder | |
| 2014/0002630 A1 | 1/2014 | Yokota | |
| 2014/0221819 A1 | 8/2014 | Sarment | |
| 2014/0275989 A1 | 9/2014 | Jacobsen et al. | |
| 2015/0005622 A1 | 1/2015 | Zhao et al. | |
| 2015/0363979 A1 | 12/2015 | Takano et al. | |
| 2016/0030131 A1 | 2/2016 | Yang et al. | |
| 2016/0030132 A1* | 2/2016 | Cheung | A61B 34/20 |
| | | | 602/42 |
| 2016/0191887 A1 | 6/2016 | Casas | |
| 2016/0220324 A1 | 8/2016 | Tesar | |
| 2016/0242623 A1 | 8/2016 | Pasini et al. | |
| 2016/0248994 A1 | 8/2016 | Liu | |
| 2016/0324580 A1* | 11/2016 | Esterberg | A61B 5/055 |
| 2017/0151432 A1 | 6/2017 | Christopherson et al. | |
| 2017/0202633 A1 | 7/2017 | Liu | |
| 2018/0042681 A1 | 2/2018 | Jagga | |
| 2018/0049622 A1* | 2/2018 | Ryan | A61B 34/10 |
| 2018/0078316 A1 | 3/2018 | Schaewe et al. | |
| 2018/0092698 A1* | 4/2018 | Chopra | A61B 90/39 |
| 2018/0140362 A1 | 5/2018 | Cal et al. | |
| 2019/0083180 A1 | 3/2019 | Ichiki | |

FOREIGN PATENT DOCUMENTS

| | | |
|---|---|---|
| JP | 2005500096 A | 1/2005 |
| JP | 200918184 | 1/2009 |
| JP | 2009524149 A | 6/2009 |
| JP | 2016503676 A | 2/2016 |
| JP | 2016512658 A | 4/2016 |
| JP | 2016158911 A | 9/2016 |
| WO | 2012075155 A2 | 6/2012 |

OTHER PUBLICATIONS

International Preliminary Report on Patentability dated Apr. 4, 2019 in corresponding/related International Application No. PCT/US2017/052411.
International Search Report and Written Opinion dated Jan. 2, 2018 in corresponding International Application No. PCT/US2017/052411.
Invitation to Pay Additional Fees dated Nov. 20, 2017 in corresponding International Application No. PCT/US2017/052411.
Mathies "Augmented reality comes to neurosurgery with tech developed by Leica" 2 pages, Aug. 6, 2016. http://www.digitaltrends.com/cool-tech/leica-captview-ar-brain-surther/#ixzz4KAChTpm8.
NewTom Cone Beam 3d Imaging product brochure, 12 pages, 2017.
ODG Smartglasses 9 product brochure, 2 pages, 2018.
Straka "A.R. Enhanced Navigated Biopsy Storyboard" Medtronic Neurosurgery, Feb. 2016, 11 pages.
International Preliminary Report on Patentability dated Jun. 18, 2020 in corresponding/related International Application No. PCT/US2018/064280.
European Office Action regarding 18822230.1, dated Nov. 8, 2022.
Examination Report corresponding to European Application No. 18822230.1, dated Aug. 9, 2023 (5 pp).
European Office Action corresponding to EP177780640, dated Dec. 23, 2022.
Korean Office Action regarding Patent Application No. 1020197010899, dated Jun. 7, 2022.
Chinese Office Action (with English translation) regarding Chinese Application No. 201180012267.3, dated Nov. 1, 2021.
Japanese Office Action (with English translation) regarding Japanese Application No. 201951598.7, dated Jul. 5, 2021.
Office Action regarding Korean Patent Application No. 10-2019-7010899, dated Oct. 6, 2021.
Chinese Office Action regarding Chinese Application No. 201880074295.3 dated Oct. 31, 2023, with English Translation, 14 pages.

* cited by examiner

SYSTEM AND METHOD FOR ASSISTING VISUALIZATION DURING A PROCEDURE

CROSS-REFERENCE TO RELATED APPLICATIONS

This application includes subject matter similar to U.S. application Ser. No. 16/210,669 filed Dec. 5, 2018. The entire disclosures of each of the above applications are incorporated herein by reference.

FIELD

The subject disclosure relates to preforming a procedure, and particularly to registering an image space to a real or subject space.

BACKGROUND

During a selected procedure, a user may acquire images of a subject that are based upon image data according to the subject. Generally the image data may be acquired using various imaging techniques or systems and the image data may be reconstructed for viewing by the user on a display device, such as a flat panel or flat screen, cathode ray tube, or the like that is positioned away from a region of operation. The region of operation may be relative to a subject, such as a human patient, for performing a selected procedure. For example, a sinus procedure may be performed and images of a subject's sinuses may be displayed on a display device that does not overlay the subject.

The procedure may further include directly viewing at least a portion of a region of interest or operation, such as with an endoscope. An endoscope may position a camera at a selected location, such as within a nasal or an accessible sinus cavity. An endoscope may have limited range of movement and/or field of view at various locations within selected anatomical areas.

SUMMARY

This section provides a general summary of the disclosure, and is not a comprehensive disclosure of its full scope or all of its features.

In various embodiments, an instrument may be positioned relative to a portion of a subject for performing a procedure. A subject may include a living subject or a non-living subject. In various embodiments, a living subject may include a human and the procedure being performed may be performed relative to a nasal passage and/or sinus cavity. For example, a balloon sinus dilation procedure may occur, such as one performed with a NuVent® EM Balloon Sinus Dilation System, sold by Medtronic, Inc. having a place of business in Minnesota. It is understood that the dilation of a sinus need not be performed with an electromagnetic (EM) navigated instrument, however the dilation of sinuses with an inflatable instrument may include instruments including various inflation and expansion features such as the NuVent® sinus dilation surgery.

In various embodiments, a procedure may occur in a region of operation of a subject. The region of operation may be a specific or limited area or volume on which a procedure is being performed or relative to which a procedure is being performed. The region of operation may also be referred to as a region of interest or include a region of interest therein. In various embodiments, for example, the sinuses of a human subject may be operated on, such as for performing debridement, dilation, or other appropriate procedures. The procedure may occur within a region of operation while a region of interest may include an entire head of the patient or cranium.

The operation performed on the sinus may generally be a low invasive or non-open procedure. In the low invasive procedure various natural body cavities such as nasal passages, are used to access the sinuses. Upon access to the sinuses, therefore, the operating end of an instrument may not be visible to a user.

The instrument that is being used to perform the procedure may include a tracking device configured or operable to be tracked by a tracking system. In various embodiments, the tracking system may include a visual or optical tracking system that tracks, such as by viewing or recording, the tracking device on the instrument. A navigation or tracking system, including a processor system, may then determine the position of the operating end relative to the tracking device based upon known and/or predetermined geometric relationships between the operating end and the tracking device.

The tracking system may include one or more cameras or optical tracking devices positioned relative to a display device. The display device may include a transparent or semi-transparent viewscreen. The viewscreen may be positioned relative to a user, such as allowing the user to view the subject through the viewscreen. The viewscreen may be mounted to a structure that allows the user to wear the viewscreen relatively close to a user's eyes such that the viewscreen fills all or a substantial portion of a field of view of the user. A displayed image may then be displayed on the viewscreen to allow the user to view the image while also viewing the subject. The tracked location of the instrument, or at least a portion thereof such as the operating end, may also be displayed on the display using the viewscreen. Accordingly, cameras may be associated with the device worn by the user to allow for a determination of a location of the instrument relative to the region of operation and/or region of interest in the region of operation and superimpose on an image or augmenting the user's view of the subject by displaying the tracked location of the instrument.

The system may include a viewing portion or system and a tracked portion. The viewing portion may view a real object (e.g. a subject) and displayed images. The viewing system, therefore, may be an augmented reality viewing system. In addition thereto, or alternatively thereto, viewing systems may include a view screen or monitor separate from or spaced away from the subject. In addition, images may be captured in real time with selected imaging systems, such as an endoscope. An endoscope may be positioned relative to the subject, such as within a nasal passage and/or sinus, and the images acquired with the endoscope may be displayed simultaneously with views of the subject that are acquired prior to an operative procedure. Therefore the viewing system may be used to display and view real time and pre-acquired images. Both types of images may be registered to the subject with various techniques, such as those described further herein.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
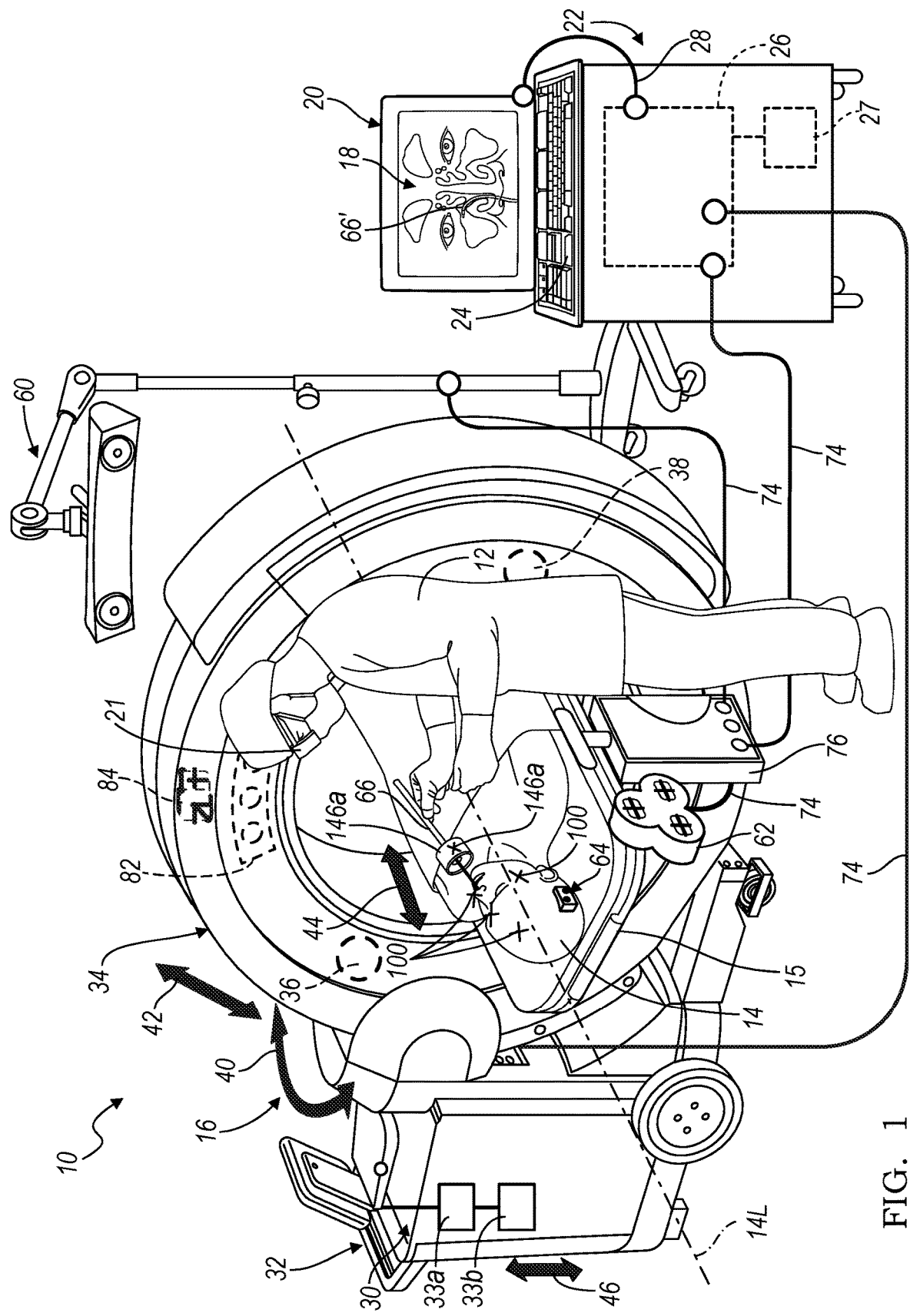
FIG. 1 is an environmental view of a user and a viewing system.

With reference to FIG. 1, in an operating theatre or operating room 10, a user, such as a surgeon 12, can perform a procedure on a subject, such as a patient 14 which may lay or be supported by a patient bed or support 15. The patient 14 may define a patient longitudinal axis 14L. To assist in performing the procedure, the user 12 can use an imaging system 16 to acquire image data of the patient 14 to allow a selected system to generate or create images to assist in performing a procedure. The imaging system 16 may include any appropriate imaging system such as a computer tomography (CT) imager, O-Arm® imaging system sold by Medtronic, Inc., and/or a NewTom® VGi evo cone beam imager sold by NewTom having a place of business in Verona, Italy.

A model (such as a three-dimensional (3D) image) can be generated using the image data. The generated model may be displayed as an image 18 on a display device 20. In addition, or alternatively to the display device 18, projection images (e.g. 2D x-ray projections) as captured with the imaging system 16 may be displayed. Furthermore, an augmented viewscreen (AV) or display device 21 may be provided to or used by the user 12. The AV 21 may be worn by the user 12, as discussed further herein. Further, the AV 21 may also be referred to as a viewing system that is an integrated system or a portion of a system for viewing various items, as discussed herein.

Either or both of the display device 20 or the augmented viewscreen 21 can be part of and/or connected to a processor system 22 that includes an input device 24 (input devices may include a keyboard, a mouse, a microphone for verbal inputs, and inputs from cameras) and a processor 26 which can include one or more processors or microprocessors incorporated with the processing system 22 along with selected types of non-transitory and/or transitory memory 27. A connection 28 can be provided between the processor 26 and the display device 20 or the augmented viewscreen 21 for data communication to allow driving the display device 20 to display or illustrate the image 18.

The imaging system 16, as discussed above, can include an O-Arm® imaging system sold by Medtronic Navigation, Inc. having a place of business in Louisville, CO, USA. The imaging system 16, including the O-Arm® imaging system, or other appropriate imaging systems may be in use during a selected procedure, such as the imaging system described in U.S. Pat. Nos. 8,238,631; 9,411,057; and 9,807,860; all incorporated herein by reference. The imaging system 16 may be used to acquire image data of the patient 14 prior to or during use of the AV 21.

The imaging system 16, when, for example, including the O-Arm® imaging system, may include a mobile cart 30 that includes a controller and/or control system 32. The control system may include a processor 33a and a memory 33b (e.g. a non-transitory memory). The memory 33b may include various instructions that are executed by the processor 33a to control the imaging system, including various portions of the imaging system 16.

An imaging gantry 34 in which a source unit 36 and a detector 38 is positioned may be connected to the mobile cart 30. The gantry 34 may be O-shaped or toroid shaped, wherein the gantry 34 is substantially annular and includes walls that form a volume in which the source unit 36 and detector 38 may move. The mobile cart 30 can be moved from one operating theater to another and the gantry 34 can move relative to the cart 30, as discussed further herein. This allows the imaging system 16 to be mobile and moveable relative to the subject 14 thus allowing it to be used in multiple locations and with multiple procedures without requiring a capital expenditure or space dedicated to a fixed imaging system. The control system may include the processor 33a which may be a general purpose processor or a specific application processor and the memory system 33b (e.g. a non-transitory memory such as a spinning disk or solid state non-volatile memory). For example, the memory system may include instructions to be executed by the processor to perform functions and determine results, as discussed herein.

The source unit 36 may be an x-ray emitter that can emit x-rays through the patient 14 to be detected by the detector 38. As is understood by one skilled in the art, the x-rays emitted by the source 36 can be emitted in a cone and detected by the detector 38. The source/detector unit 36/38 is generally diametrically opposed within the gantry 34. The detector 38 can move in a 360° motion around the patient 14 within the gantry 34 with the source 36 remaining generally 180° opposed (such as with a fixed inner gantry or moving system) to the detector 38. Also, the gantry 34 can move isometrically relative to the subject 14, which can be placed on the patient support or table 15, generally in the direction of arrow 40 as illustrated in FIG. 1. The gantry 34 can also tilt relative to the patient 14 illustrated by arrows 42, move longitudinally along the line 44 relative to the longitudinal axis 14L of the patient 14 and the cart 30, can move up and down generally along the line 46 relative to the cart 30 and transversely to the patient 14, to allow for positioning of the source/detector 36/38 relative to the patient 14. The imaging device 16 can be precisely controlled to move the source/detector 36/38 relative to the patient 14 to generate precise image data of the patient 14. The imaging device 16 can be connected with the processor 26 via connection 50 which can include a wired or wireless connection or physical media transfer from the imaging system 16 to the processor 26. Thus, image data collected with the imaging system 16 can be transferred to the processing system 22 for navigation, display, reconstruction, etc.

The source 36 may be any appropriate x-ray source, such as a multiple power x-ray source. It is understood, however, that the imaging system 16 may be any appropriate imaging system, such as a magnetic resonance imaging (MRI) system, C-arm x-ray imaging system; computed tomography (CT) imaging system, etc. The image data and/or images acquired with the selected imaging system, however, may be displayed on one or more of the display devices 20, 21.

It is further understood that the imaging system 16 may be operated to acquire image data and/or images prior to performing a procedure on the patient 14. For example, images may be acquired and studied to diagnose and/or plan a procedure for the patient 14. Thus, the user 12 that performs a procedure on the patient 14 need not use the imaging system 16 in the same room as the procedure being performed.

According to various embodiments, the imaging system 16 can be used with a tracking system and navigation system, including various portions as discussed herein, operable to track a location of the imaging device 16 and/or other portions. The tracking system may include a localizer and/or digitizer, including either or both of an optical localizer 60 and an electromagnetic localizer 62 can be used to generate a field and/or receive and/or send a signal within a navigation domain relative to the patient 14. A navigated space or navigational domain relative to the patient 14 can be registered to the image 18. Correlation, as understood in the art, is to allow registration of a navigation space defined within the navigational domain and an image space defined by the image 18.

In various embodiments, a patient tracker or dynamic reference frame 64 can be connected to the patient 14 to allow for a dynamic tracking and maintenance of registration of the patient 14 to the image 18. The patient tracking device or dynamic registration device 64 allows for images to be registered and then used for a selected procedure. In various embodiments, the localizers 60, 62 may track the patient tracker. Further communication lines 74 may be provided between various features, such as the localizers 60, 62, the imaging system 16, and an interface system 76 and the processor system 22, which may be a navigation processor system. In various embodiments, the communication system 74 may be wired, wireless, or use a physical media transfer system (e.g. read/write to a memory chip).

Further, the gantry 34 can include a tracking device, such as an optical tracking device 82 or an electromagnetic tracking device 84, to be tracked, such as with one or more of the optical localizer 60 or electromagnetic localizer 62. Accordingly, the imaging device 16 can be tracked relative to the patient 14 as can the instrument 66 to allow for initial registration, automatic registration, or continued registration of the patient 14 relative to the image 18. Registration and navigated procedures are discussed in the above incorporated U.S. Pat. No. 8,238,631, incorporated herein by reference.

One skilled in the art will understand that the instrument 66 may be any appropriate instrument, such as a ventricular or vascular stent, spinal implant, neurological stent or stimulator, ablation device, dilator, or the like. The instrument 66 can be an interventional instrument or can include or be an implantable device. Tracking the instrument 66 allows for viewing a location (including x,y,z position and orientation) of the instrument 66 relative to the patient 14 with use of the registered image 18 without direct viewing of the instrument 66 within the patient 14.

Figure 2A:
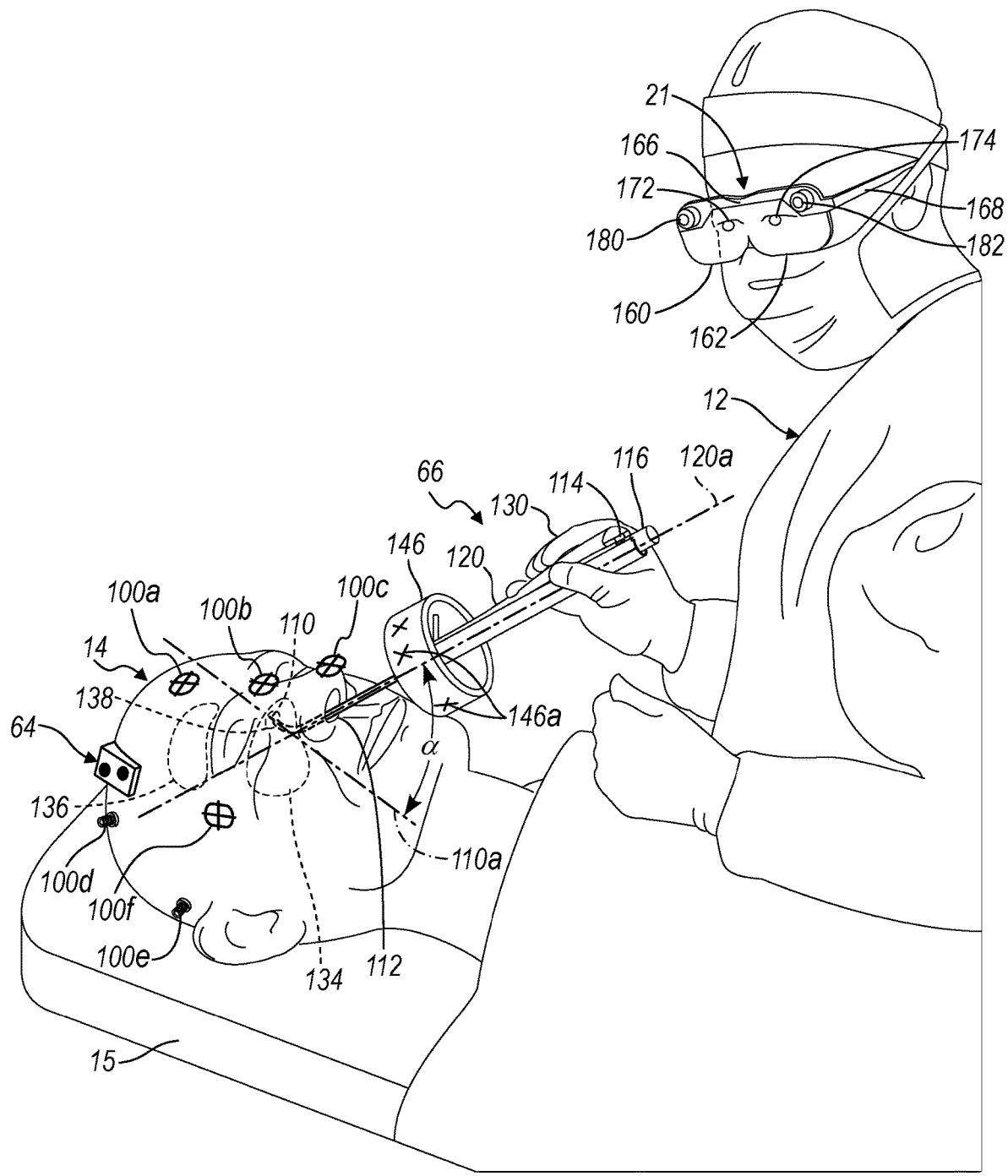
FIG. 2A is a real/physical world view of a region of interest including an instrument, according to various embodiments.

With continuing reference to FIG. 1 and additional reference to FIG. 2A, the patient 14, in addition to and/or alternatively to the patient tracker 64, may include one or more patient markers or trackers 100 (herein referenced to 100 and a lowercase letter). The patient trackers 100 may include various features such as being opaque or imageable with various imaging systems, such as X-rays or MRI. The trackers 100, according to various embodiments, may generally be visible or captured in the image data acquired with the imaging system 16, according to various embodiments. Thus, the patient markers 100 may be identifiable in an image or image data of the subject 14.

In various embodiments, the patient markers 100 may be identified substantially automatically by the processor system 26 and/or 33a, or any other appropriate imaging processor or processor system. The markers 100 may include a selected and/or unique geometry that may be identified in the image or image data. Various techniques may be used to segment and identify the markers 100 in the selected image or image data. It is also understood, however, that the user 12 may identify the markers in the image data such as by selecting portions in the image and identifying the portions as the markets 100 with one or more of the user inputs 24.

The markers 100 may be positioned on the patient 14 in any appropriate manner. For example, the markers 100 may be adhered to the patient 14 such as with a self-adhesive backing, an appropriate glue or adhesive material added to the marker 100 and/or the patient 14, or other appropriate mechanism. Further, or in addition thereto, the markers 100 (e.g. the markers 100d and 100e) may be fixed to a bony structure of the patient 14. The markers 100 may be formed or provided as screws or have threaded portions that allow them to be threaded and fixedly positioned into a bone structure, such as a cranium of the patient 14.

Regardless of the connection technique, the markers 100 are positioned on the patient 14 at a selected time. Generally the markers 100 are positioned on the patient 14 prior to imaging, such as acquiring image data or images of the patient 14 with the imaging system 16. Therefore when the image system 16 is operated to acquire images of the patient 14, the markers 100 are positioned on the patient 14 and will appear in any acquired image data or images.

The markers 100 may, therefore, be used as fiducial points. It is understood that the patient 14 may also include various physical and anatomical fiducial points, such as a tip of the nose, corner of an eye, earlobe, or the like. Nevertheless, the fiducial points, whether provided by the markers 100 and/or an anatomical fiducial point to the patient 14, may be used for registration of the images acquired with the imaging system 16. It is understood by one skilled in the art, images acquired to the patient 14 may define an image space. The image space may be of a region of operation or procedure (RO) and/or an area greater than, but at least including, the RO, such as referred to as a region of interest (ROI). It is understood that a procedure may occur in a specific area in a region of interest. Nevertheless coordinates of the image data or space may be correlated or registered to the patient 14 in a physical or real space. The markers 100 may be used to register the image space to the patient and/or navigation space as defined by the patient 14 and/or a region of operation within or relative to the patient 14.

The instrument 66, as noted above, may be any appropriate instrument. The instrument 66 may include a dilator instrument that includes a distal end 110 that may be positioned within a portion of the patient 14, such as through a nasal passage 112 and into one or more sinuses of the patient 14, such as the frontal sinus. The instrument 66 may further include a proximal end 114 to which a connector 116 to which an inflation system (not illustrated) may be connected, such as to a connector or a nipple. The connector 116 may allow for material to be passed through the instrument 66, such as a handle 120, into a balloon or other expandable portion 122 at or near the distal end 110 of the instrument 66.

Inflation of the balloon 122 may, as is generally understood by one skilled in the art, expand to dilate or expand a portion of the sinus.

In various embodiments, the user 12 may grasp the instrument 66 such as with a hand 130. The user 12 may then move the instrument 66 relative to the patient 14, such as within the patient 14, such as to move the instrument distal end 110 into a sinus, such as a maxillary sinus 134. It is understood, however, that various instruments, including the instrument 66, according to various configurations may also be used to access one or more portions of other sinuses of the patient 14 such as a frontal sinus 136 and/or a sphenoid sinus 138.

The instrument 66 may further include a tracking device 146. The tracking device 146 may be affixed to the instrument 66, such as the elongated handle portion 120. Generally the tracking device 146 is substantially fixed relative to the handle 120 such that movement of the handle 120 by the user 12, such as with the users hand 130, moves the handle 120 and the tracking device 146. According to various embodiments, the tracking device 146 is also rigidly fixed in space relative to the distal end 110 of the instrument 66. Accordingly, knowing the position (e.g. location and/or orientation) of the tracking device 146 will allow for knowing the position of the distal end 110. Further, the distal end 110 may extend along an axis 110a that is at an angle 150 relative to an axis 120a of the handle 120. Accordingly, the tracking device 146 may be positioned and have a known or predetermined position and geometry relative to the distal end 110 to be tracked to determine the position of the distal tip 110 relative to the tracking device 146 that is affixed to the handle 120.

Figure 2B:
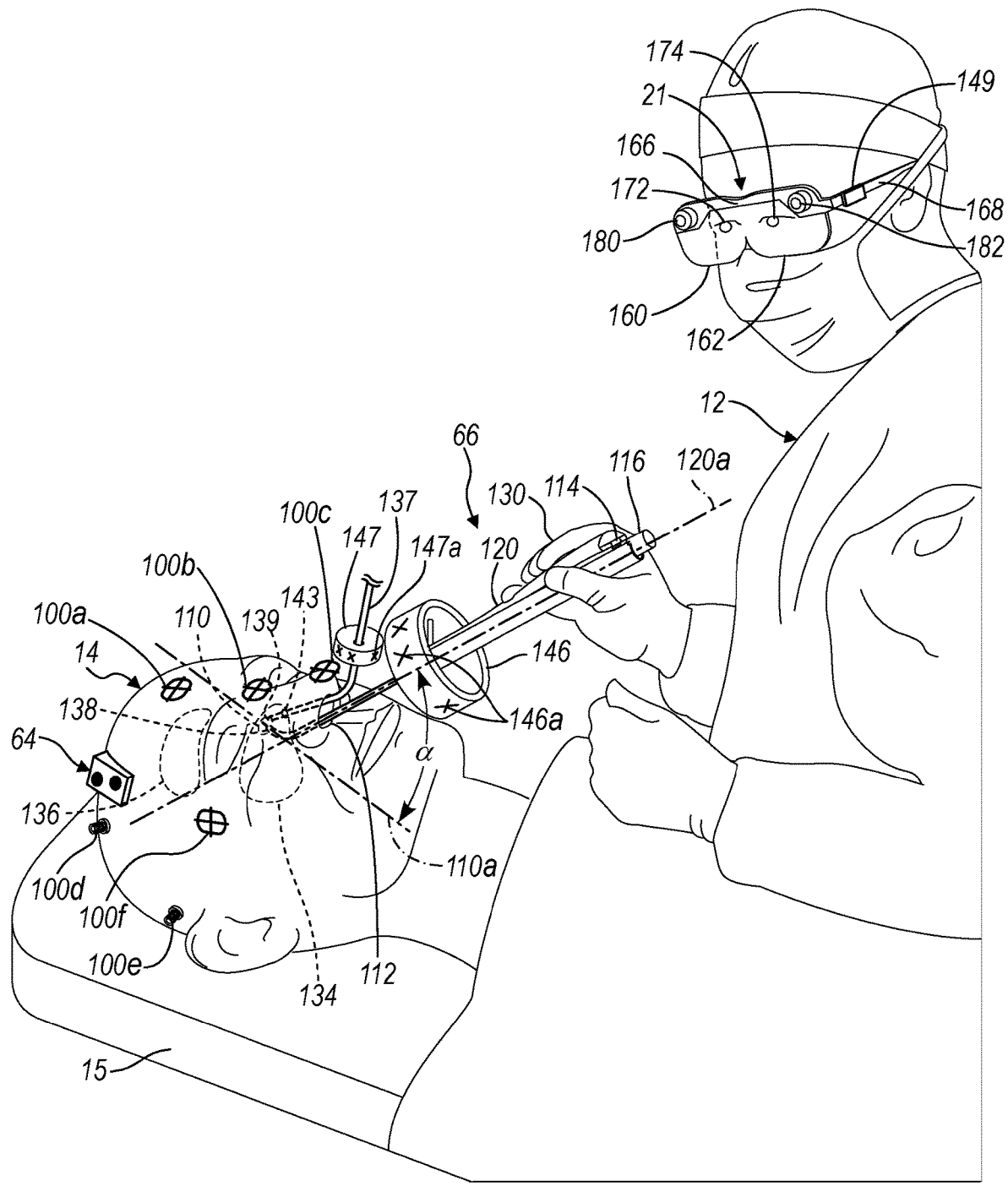
FIG. 2B is a real/physical world view of a region of interest including instruments, according to various embodiments.

In addition to the instrument 66 that may be used by the user 12, additional instruments may also be used relative to the subject 14. For example, as illustrated in FIG. 2B, the user 12 may include or operate an imaging system 137. The imaging system 137 may include a distal image capturing portion 139, such as a camera lenses or camera. The imaging instrument 137 may generally be understood to be an endoscope, such as a EVIS EXERA III endoscope, sold by Olympus America. The endoscope 137 may be positioned relative to the subject 14 by the user 12, according to various generally known techniques and embodiments. The image gathering portion 139 may image various portions of the subject 14, such as internal portions of the subject 14 including the sinus cavity 134, or other appropriate portions, including the nasal passage 112. As discussed further herein, the endoscope 137 may capture images that may be in substantially real time, such as during positioning of the instrument 66 within the subject 14. The real time images captured with the endoscope 137 may be displayed on various display devices or view systems, such as the display device 20 and/or the AV 21. Therefore, the endoscope 137 may be used to capture images at the imaging portion or end 139 and display the images according to generally known techniques. The images may be transmitted through various systems, such as wirelessly or wired transmission systems, to the processing system 22 for display on the selected display or viewing systems, including the display device 20 and/or the AV 21. The signal from the endoscope 137 may be a digital signal and/or an analogue signal and may be transmitted directly from the endoscope and/or through the interface system 76. Regardless, the images acquired at the imaging portion 139 of the endoscope 137 may be viewed by the user 12 and/or any other appropriate individual. Further, the images may be captured and recorded for various purposes.

The endoscope 137, as discussed above, may be used to acquire images of the subject 14. To assist in acquiring the images or in performing a procedure, the position of the endoscope, particularly the position of the images being acquired, may be determined by one or more tracking devices. For example, an endoscope tracking device 147 may be incorporated onto the endoscope 137 similar to the tracking device 146 connected to the instrument 66, as discussed above. The tracking device 147 may include one or more viewable markers or portions 147a, similar to the markers 146a on the tracking device 146. As discussed herein, therefore, the tracking device 147 may be viewed or imaged with the AV 21 to be tracked by the selected tracking system as discussed further herein. The tracking device 147 may be used to determine the position of the end 139 capturing images to assist in determining a location of the image within the patient 14. The endoscope 137 may be positioned within the subject 14, such as in the sinus cavity 134 that is not directly viewable by the user 12. Additional and/or alternative tracking devices may include an end tracking device 143 that may be positioned or incorporated into the endoscope 137 at or near the image capture end 139. The tracking device 143 may be similar to the tracking device 64, discussed above. The tracking device 143 may be an optical tracking device, EM tracking device, ultrasound tracking device, or other appropriate tracking device. As discussed further herein, registration of the instrument 137, such as with the tracking device 143, and the patient or subject tracker 64 may be used to assist in registering and maintaining registration of the endoscope 137 relative to the subject 14.

The user 12 may also have and/or use the alternative or augmented viewscreens or viewing system 21 for use during the procedure. The AV 21 may be an appropriate device that includes at least one viewscreen and generally two viewscreens including a first viewscreen 160 and a second viewscreen 162. The viewscreens may be fixed to a frame member 166 that may have one or more temple members 168 to allow the AV 21 to be worn by the user 12 in a similar manner to eyeglasses. Therefore, the viewscreens 160, 162 may be positioned generally in front of, respectively, both eyes 172 and 174 of the user 12. In this manner images may be displayed on one or both of the viewscreens 160, 162 to allow the user 12 to view images. The AV 21 may include one or more various devices and systems such as the Hololens® wearable computer peripherals sold by Microsoft Corporation, R-9 Smartglasses wearable computer peripherals sold by Osterhout Design Group, having a place of business in San Francisco, California, and/or DAQRI Smart Glasses® wearable computer peripherals sold by DAQRI having a place of business at Los Angeles, California.

In various embodiments, the viewscreens 160, 162 may also be substantially transparent except for the portion displaying an image (e.g. an icon or rendering). Therefore, the user 12 may view the patient 14 and any image displayed by the viewscreens 160, 162. Moreover, due to the two viewscreens 160, 162 displaying selected images, the display may be perceived to be substantially stereoscopic and/or three-dimensional by the user 12 relative to the patient 14. As discussed further herein, therefore, the user 12 may view the patient 14 and an image when performing a procedure.

The AV 21 may also include one or more cameras, such as a first camera 180 and a second camera 182. The two cameras 180, 182 may be used to view the region of interest, such as a head of the patient 14. As illustrated in FIG. 2A the user 12 may view substantially a head portion and a neck portion of a patient when performing a procedure in a region of operation, such as in a sinus of the patient 14. Therefore the cameras 180, 182 may also view the patient 14, for various purposes, as discussed further herein. Moreover, the cameras may view other objects in the region of interest such as the tracking device 146 on the instrument 66 and/or the markers 100. The tracking device 146 may include one or more viewable markers or portions 146*a* that are viewable by the cameras 180, 182 to be used to determine a perspective or view of the tracking device 146 by the AV 21.

While the use of two cameras 180, 182 are disclosed and discussed herein to view and determine the location of the tracking device 146 and/or markers 100, it is understood by one skilled in the art that only one camera, such as only one of the cameras 180, 182 may be required for tracking, as discussed herein. Based on various features (e.g. shapes, images, etc.) on the tracking device 146, tracking device 147, and/or the markers 100 a single camera, such as the camera 180, may be used to determine the location (i.e. x, y, z coordinates and orientation) relative to the camera 180 and/or relative to other trackable items. For example, the camera 180 may be used to determine the relative location of the tracking device 146 (and therefore the instrument 66) relative to the markers 100. Further, the camera 180 may be placed at any location relative to the user 12, such as on a head of the user 12 separate from the AV 21. The camera 180, however, may still remain in communication with the processor system 22 for display of various images on one or more of the viewscreens 160, 162.

The AV 21 including the cameras 180, 182, therefore, may view the markers 100 on the patient 14 in combination with the tracking device 146 on the instrument 66. The markers 100 on the patient 14 may be viewed by the cameras 180, 182 and may be identified by the user 12 and/or substantially automatically by executing instructions on a processor system, such as by executing instructions with the processor 26.

As discussed above, the processor system 22 may have access to instructions, such as those saved on the memory 27, to assist in identifying the markers 100 in an image. The cameras 180, 182 may have a field of view that includes the region of interest including the head of the patient 14 and also viewing the markers 100. The instructions, which may be included in selected software, may identify the markers 100 in a viewed image, such as by segmentation of the image and identifying a selected shape, density, color, or like of the markers 100.

Once the markers 100 are identified, images acquired with the imaging system 14 may be registered, such as with the processor system 22, to register the images including the markers 100 therein in the field of view of the cameras 180, 182 of the AV 21. A registration may occur by matching the identified markers 100 in the image data acquired by the image device 16 and the markers 100 in the field view image acquired with the cameras 180, 182 of the AV 21. The markers 100 are generally maintained in the same position on the patient during acquisition of image data with the imaging system 16 and when in the field of view of the cameras 180, 182 during the procedure. Registration may also occur due to the tracking device 143 on the endoscope 137 and the patient tracker or dynamic reference frame 64. As discussed above, registration may occur due to various registration techniques, such as those disclosed in U.S. Pat. No. 8,238,631, incorporated herein by reference. Registration may be made by tracking the tracking device 143 (associated with the endoscope 137) and/or the patient tracker 64. Further, the AV 21 may include a tracking device 149 that may allow the AV 21 to be tracked in a same or similar tracking system and/or frame of reference relative to the subject or dynamic reference frame 64 and/or the tracker 143 on the endoscope 137. Thus, the AV 21 may be registered relative to the endoscope 137 and/or the subject 14. This image is acquired with the endoscope 137 may be used to be displayed relative or for viewing by the user 12 relative to a view of the user 12, as discussed further herein.

As discussed above, in reference to FIG. 2A and FIG. 2B, image data and/or images acquired with the imaging system 16 where the markers 100 are connected to the patient 14 will include data of the markers 100. The markers 100 may be identified in the image data or images acquired with the imaging system 16 as discussed above. The markers 100 may also be viewed by the cameras 180, 182 associated with the AV 21. The cameras 180, 182 may also view the patient 14 to identify or assist in identifying anatomical fiducial markers. Nevertheless, the markers 100 identified in the image data acquired with the imaging system 18 may also be identified in images acquired with the cameras 180, 182. It is understood by one skilled in the art, the images acquired with the cameras 180, 182 may be any appropriate type of images, such as color images, infrared light images, or the like. Nevertheless, matching of the markers 100 identified in the image data acquired with the imaging system 16 may be matched to locations identified of the markers viewed with the cameras 180, 182 to register the space or field of view viewed by the AV 21 to the image space of images acquired with the imaging system 16. As discussed further herein, therefore, images or portions of images acquired with the imaging system 16 may be displayed with the viewscreens 160, 162 as appearing to be superimposed on the patient 14.

The subject 14 may also be registered relative to currently acquired images or real time images acquired with the endoscope 137 due to the subject tracker 64 and the tracker 143 on the endoscope 137. Registration may be made to the subject 14 such as with the fiducial markers 100*d* and/or other fiducial features. Thus, the real time images acquired with the endoscope 137 may also be registered to the pre-acquired images. Thus the pre-acquired images may be registered to the instrument 66 such as with the cameras 180, 182 and/or to the AV 21 via the AV 21 tracker 149. Thus images acquired with the endoscope 137 may be registered to pre-acquired images of the subject 14 and for viewing by the user 12, such as with the AV 21.

Figure 3A:
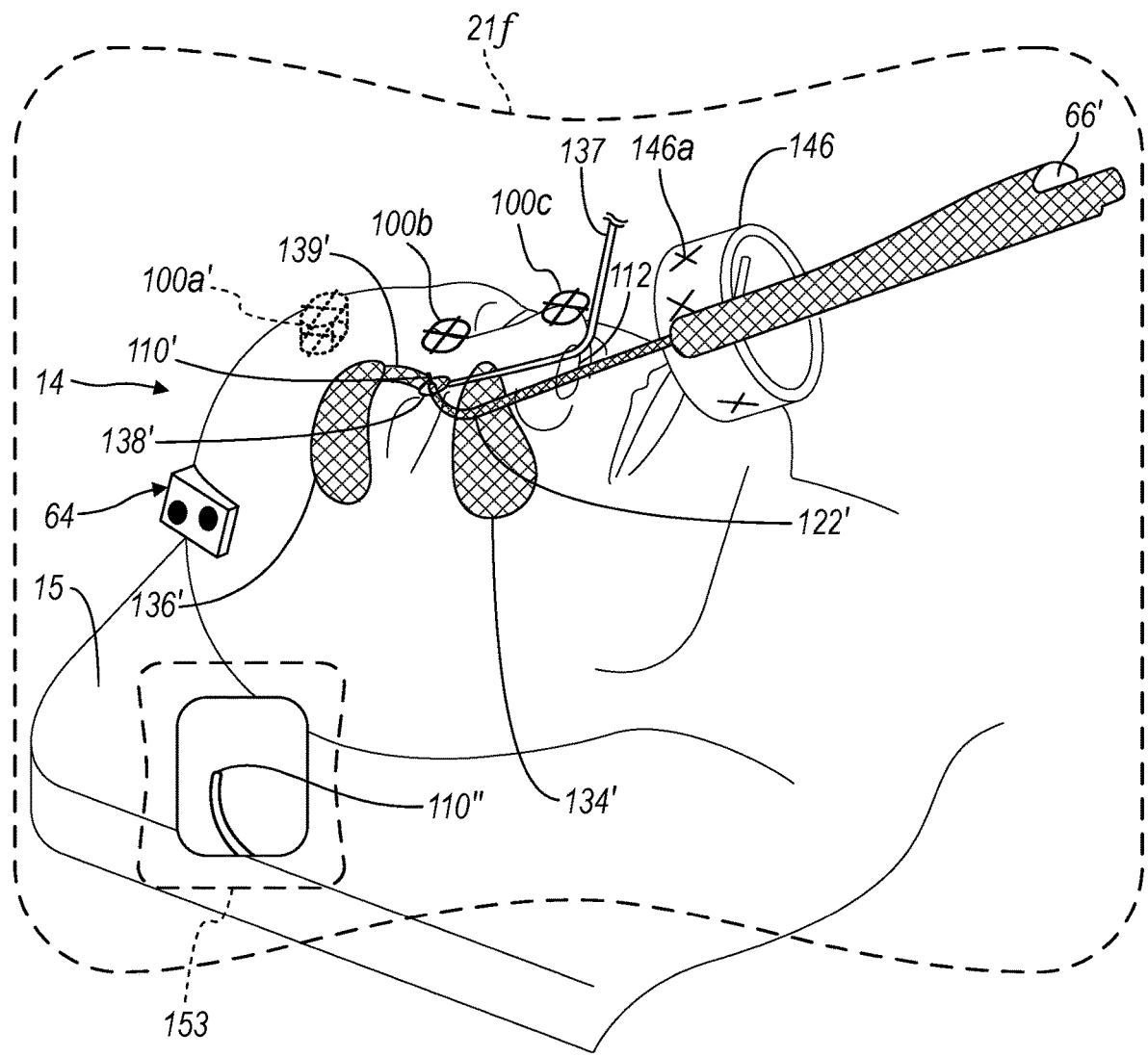
FIG. 3A is a view point of a user viewing the real/physical world and at least one displayed icon, according to various embodiments.
Figure 3B:
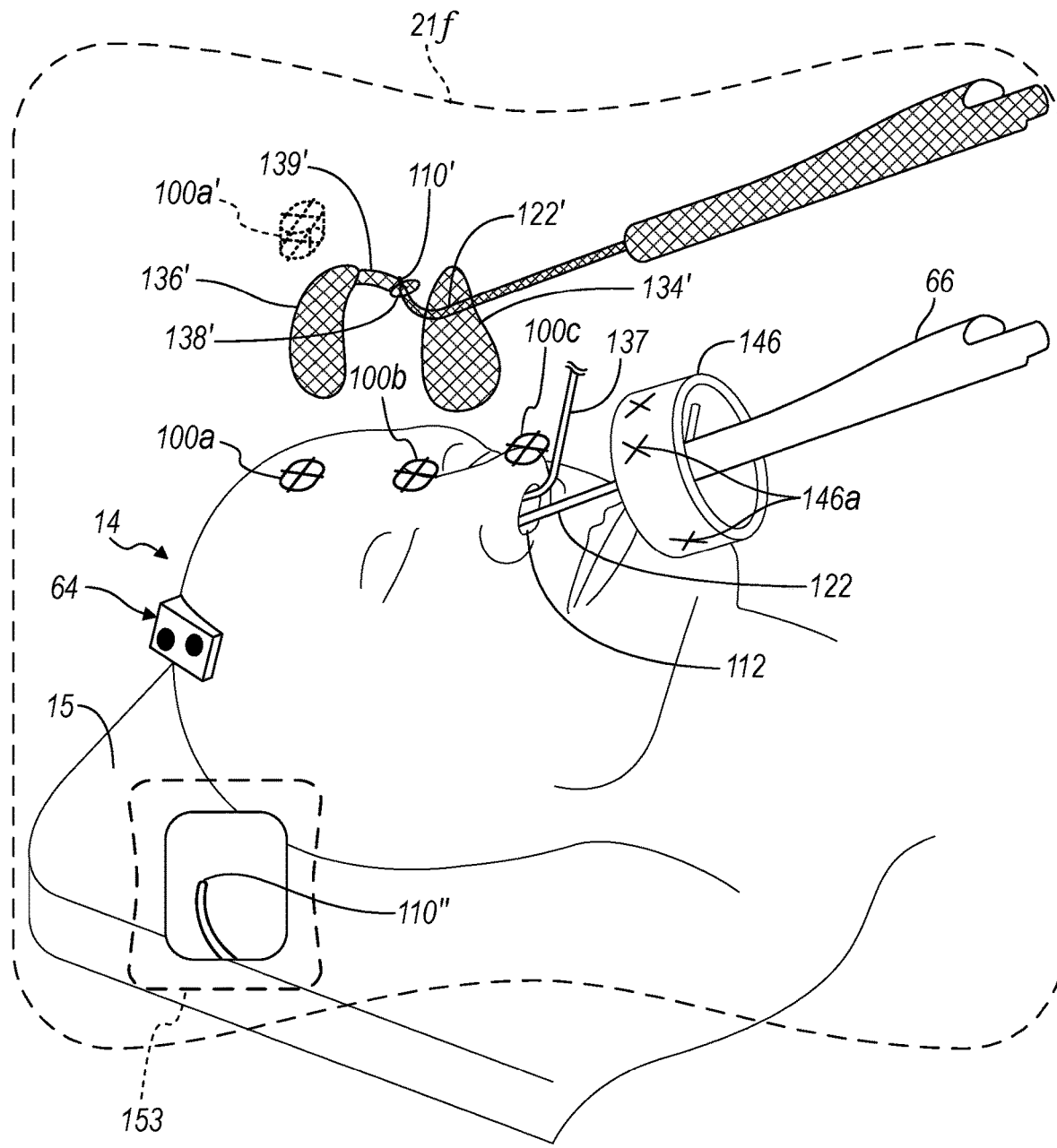
FIG. 3B is a view point of a user viewing the real/physical world and at least one displayed icon, according to various embodiments.

The user 12 may view the subject 14 through the AV 21, as illustrated in FIG. 3A and FIG. 3B. The user 12 may view or have a field of view 21*f*, as illustrated by dash-lines in FIG. 3A and FIG. 3B. The field of view 21*f* may represent a view by the user 12 through the AV 21 when viewing the subject 14, or any area through the AV 21. Thus, the user 12 may view the subject 14, that is real or physical, and the view may also be augmented by graphical representations (also referred to herein as icons) that are displayed by the AV 21. The icons or graphical representations may be displayed in the field of view 21*f* for viewing by the user 12 when viewing the field of view through the AV 21.

In addition to the icons, as discussed further herein, additional images or image areas 153 may be displayed within the AV field of view 21*f* to be viewed by the user 12. The supplemental viewing areas 153 may be used to display various images or information for use or viewing by the user 12. For example, the real time images acquired by the endoscope 137 may be displayed in the auxiliary or augmented viewing area 153. Thus, the user 12 may view the subject 14 in the field of view 21*f* to view the subject 14, the various graphical representations as discussed further herein, and additional images (e.g. endoscopic images) in the auxiliary or additional viewing area 153. The user 12 may also selectively select or choose information to be displayed in the auxiliary display area 153 such as pre-acquired images, the real time images with the endoscope, or other appropriate information.

With additional reference to FIG. 3A and FIG. 3B, for example, sinuses such as the maxillary sinus 134 may be displayed as a maxillary sinus icon 134'. FIG. 3A is an illustration of a point of view of the user 12 viewing through the AV 21 the patient 14 and various portions that are displayed with the viewscreens 160, 162. As discussed above, therefore, the maxillary sinus icon 134' may be displayed for viewing by the user 12 as if the user 12 could see into the patient 14 and view the maxillary sinus 134. The maxillary icon 134' may be graphical rendering of the image data or an artificially created icon to represent the maxillary sinus.

It may also be selected to illustrate other portions of the anatomy of the patient 14 such as the frontal sinus 136 and one or more of the sphenoid sinuses 138. The user 12 may also view any real world object, such as the patient 14 and/or the markers 100 affixed to the patient 14. The user may also view other real world portions, such as the patient support 15. Therefore the user 12 may view both features superimposed on the patient 14 due to the viewscreens 160, 162 and items in the real world by viewing through transparent portions of the viewscreens 160, 162.

Further, the cameras 180, 182 may view the tracking device 146. By viewing the tracking device 146 the cameras 180, 182 may determine the position of the tracking device 146 relative to the markers 100. The position of the markers 100 are placed on the patient 14 to identify locations of the patient 14. The known position of the instrument tracking device 146 relative to one or more of the markers 100 allow for a determination of a portion of the instrument 66 relative to the tracking device 146 and the patient 14. As discussed above, the distal end 110 of the instrument may be at a known and fixed position relative to the tracking device 146. The known and fixed relative position (e.g. the geometry) of the distal end 110 relative to the tracking device 146 may, therefore, be stored in the memory 27 or other appropriate memory.

The tracked location of the tracking device 146, may be determined by triangulating the location of the tracking device 146 based on a "view" of the tracking device with one or more of the cameras 180, 182. The processor system 22 may execute instructions, as generally understood in the art, to then determine the position of the distal end 110 and/or the working portion such as the inflatable member of 122 and an instrument icon may be illustrated to include or illustrate the various portions relative to the patient 14 by displaying it on the viewscreen 160, 162. The instructions that are executed by the processor system 22 may include instructions stored and recalled from the memory 27. The instructions may include those that are based on an algorithm to triangulate the location of the viewed portion, such as the tracking device 146, based on separate views from the two cameras 180, 182. The separate views may be used to generate signals from the two cameras 180, 182 (e.g. including image data) and the signals may be transmitted to the processor system 22. Triangulation of the location of the tracking device 146 may be based on a known distance between the two cameras 180, 182 and each separate view captured by each of the two cameras 180, 182.

Accordingly, the viewscreens 160, 162 may include a graphical representation also referred to as an icon 110' of the distal end and/or an icon 122' of the inflatable portion of the instrument 66. The icon, such as the distal icon 110' may be illustrated as an icon on one or more of the viewscreens 160, 162 such as it appears to be superimposed or displayed relative to the patient 14. It is understood that an icon of more than a portion of the instrument 66 may be used, therefore, an instrument icon 66' may be illustrated as the entire instrument including all portions of the instrument 66.

The AV 21 may be in communication with the processor system 22 and/or may include onboard processing and/or other communication features to communicate with other processor systems. Accordingly, the view of the region of interest, such as the head of the patient 14, by the cameras 180, 182 of the AV 21 may be transmitted to the processor system 22. Due at least to the spacing apart of the cameras 180, 182, a triangulation may be determined for each viewed point in space, such as the markers 100 and/or the tracking device 146, relative to the cameras 180, 182. A relative location of the tracking device 146 to one or more of the markers 100 may be determined such as by executing instructions with the processor system 22.

The processor system 22 receiving images from one or both of the two cameras 180, 182 may process and determine the distance between the various tracked, or any viewed, portions such as the markers 100 and the tracking device 146. The processor system 22, therefore, executing instructions accessed in the memory 27 may then provide to the viewscreens 160, 162 the selected and/or appropriate image portions such as the instrument icon 66' or portions thereof and/or other imaged features, such as icons representing the sinuses including the frontal sinus 136' or other appropriate portion from the image data. The registration of the pre-acquired images, such as those acquired with the imaging system 16, based upon the tracked location of the tracking device 146 and/or the markers 100 may be based upon known registration techniques such as those disclosed in the U.S. Pat. No. 8,238,631, incorporated herein by reference. The registration may be substantially automatic and/or based upon identification of fiducial markers, such as the markers 100, in the images 18 and/or the markers 100 on the patient 14.

The user 12, therefore, may view both the patient 14 and other features, such as the instrument icon 66', relative to the patient 14 based upon the viewscreens 160, 162. The cameras 180, 182 may provide all of the tracking information relative to the user 12 and the patient 14 for determining a location of various portions of the instrument 66, such as the distal tip 110 for displaying them with the viewscreens 160, 162. The perception of the user 12 may be that the instrument 66 is viewable relative to the patient 14 even though it is within the patient 14. Further, the image data acquired with the imaging system 16 may be displayed as features, such as icons, with the viewscreens 160, 162 relative to the patient 14. Again, the perception by the user 12 of the patient 14 may be that the various portions, such as the sinuses 134, 136, 138, are viewable by the user 12 due to the AV 21. Accordingly, as illustrated in FIG. 3A, the view of the patient 14 may be augmented to illustrate features that are otherwise un-viewable by the user 12 with the users 12 regular vision. In other words, the user 12 may view the patient 14, as illustrated in FIG. 3A in physical space, and a representation of an area within the patient 14, such as with the icons or renderings discussed above. This view may also be 3D and change in perspective as the user moves relative to the patient 14 and/or the instrument 66.

The patient 14 may be viewed through the view screens 160, 162 as specifically illustrated in FIG. 3A. The various icons, such as the maxillary icon 134' and the sphenoid icon 138' may be displayed relative to the icon 66' of the instrument 66. The icons may have various and selected opacities and/or cutaways for viewing of the instrument icon 66' relative to the anatomy icons, such as the sphenoid icon 138'. Accordingly, the user 12 viewing the field of view including the icons, such as the sphenoid icon 138' and the instrument icon 66' may see both the icons simultaneously. Moreover the user 12 may perceive a position of the instrument 66 within the selected sinus, such as the sphenoid sinus 138, by viewing the instrument icon 66' and the sinus icon, such as the sphenoid sinus icon 138', substantially simultaneously. In other words, the opacity of various icons, such as the sinus icons, may be selected to have a transparent view to be able to view the instrument icon within or as if it is within the selected anatomical portion. This allows the user 12 to view the patient 14 and the icons of the instrument and the anatomy substantially simultaneously and as if present on the patient 14, as illustrated in FIG. 3A.

In addition to, or alternatively thereto, the various icons may be displayed at a position away from the patient 14. For example, as illustrated in FIG. 3B, the instrument icon 66' may be displayed away from the patient 14 although at a tracked and determined location relative to an anatomical portion icon, such as the sphenoid icon 138'. It may be selected to illustrate only those anatomical portions that are interacting or having been passed through by the instrument 66 therefore all icons may not be necessarily to be shown. It is understood that various pathways, such as an icon pathway 139' (See FIG. 3A and FIG. 3B) between various potions of the anatomy, such as through the nasal passage 112 even when the instrument 66 is within the nasal passage 112 and obscured from a non-augmented view of the user 12. Therefore, as illustrated in FIG. 3B, it is understood that the displayed portions of the anatomy that are represented or based upon the image data acquired of the patient 14 may be displayed at a location away from the respective and relative physical location on the patient 14. Accordingly the icons, such as the sinus icons may be displayed at a distance away from the patient 14. This may allow the user 12 to have a more and/or substantially unobstructed view of the patient 14 while also being able to view the relative location of the instrument 66 relative to selected anatomical portions.

Moreover the view screens 160, 162 may be used to display other images such as an endoscopic image that may be acquired substantially simultaneously and in real time, if selected. That is, the user 12 may place an endoscope in the nasal passage 112 as well and one or more of the viewscreens 160, 162 may display the endoscope view. Accordingly, it is understood that the user 12 may position an endoscope through the nasal passage 112 with the instrument 66 to provide a real time and endoscopic point of view which also may be displayed on the view screens 160, 162 and relative to selected icons, such as the sinus icons and/or the instrument icon 66'.

Moreover, it is understood that various images may be displayed on both of the view screens 160 and 162 or only one of the view screens 160, 162. It will be understood that images displayed on the two view screens 160, 162 may be substantially similar, but altered to allow for a perception of depth and/or three-dimensionality of the selected portions, such as of the sinuses and/or the instrument 66 either based upon the image data and/or icons, by the user 12. Accordingly, the displays 160, 162 may have identical displays, substantially different displays or only one display per view screen, or be similar to provide a perception of depth for viewing by the user 12.

As discussed above, the auxiliary image 153 may show or illustrate the position of the instrument 66, such as a distal end image 110" illustrated in the auxiliary image 153. The auxiliary image 153 may be the real time image acquired with the endoscope 137, as discussed above. The distal end image 110", therefore, may also be a real time image of the instrument 66. The auxiliary image 153 may also display a surface of the anatomy, such as within the sinuses, for viewing by the user 12 during a selected procedure. Therefore the field of view 21*f* may allow the user 12 to view the subject 14, graphical representations of instruments displayed relative to and/or superimposed on the subject 14, pre-acquired images of the subject displayed relative thereto and/or superimposed on the subject 14, and/or auxiliary images such as real time images of the instrument 66. Thus the user 12 may select which images to view in the field of view 21*f*. It is understood that any of the images or graphical representations may also be displayed on various other display devices, such as the display device 20. The display device 20 may also view or display both the graphical representations of the locations of the instrument 66, pre-acquired images, and real time images, either alone or in combination.

Figure 3C:
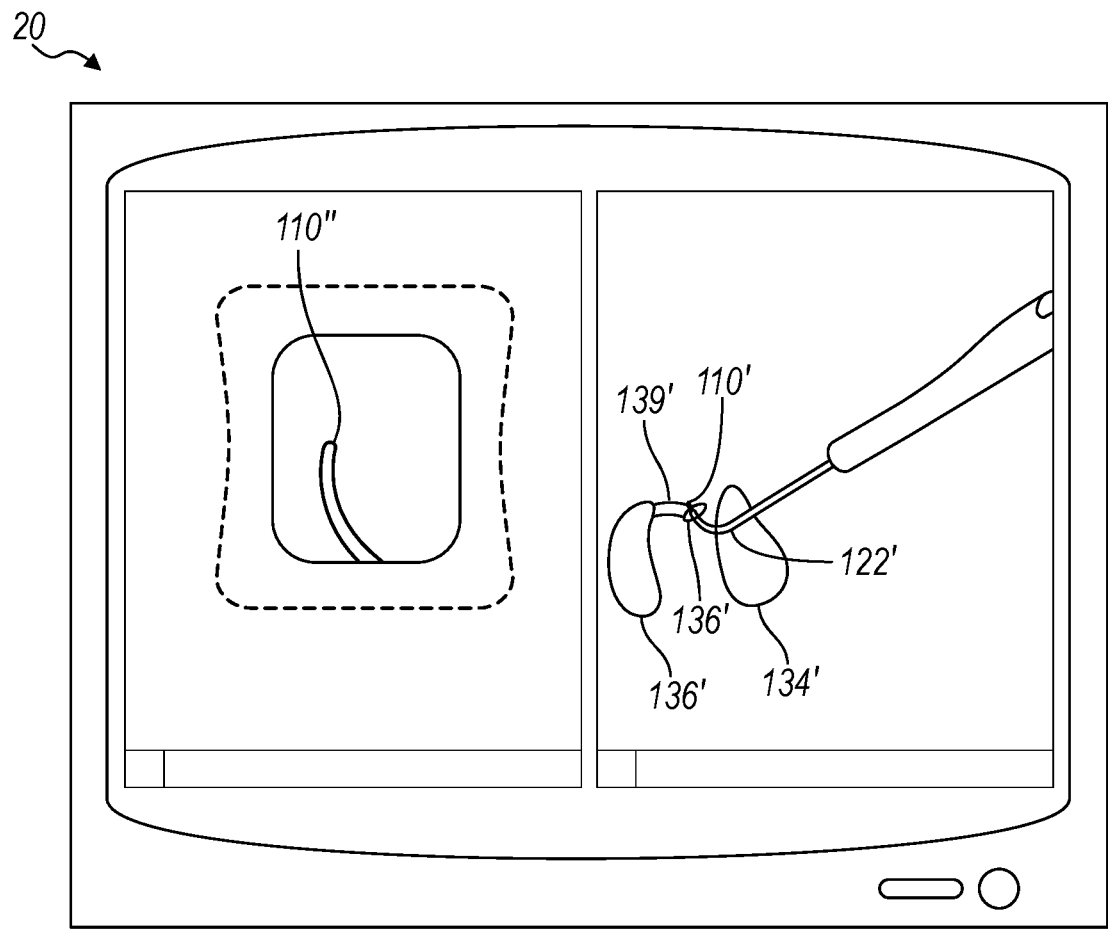
FIG. 3C is a display of a view point of a user viewing at least one displayed icon and a real time image with a display device, according to various embodiments.

With reference to FIG. 3C, the field of view may also be displayed with the display device 20. In various embodiments, the view of the endoscope may be displayed as an auxiliary view 153' on the display 20. The icons 110' and the portions of the anatomy, such as the sinus 134', may also be display with the display device 20. The graphical representations may be substantially three-dimensional (3D) when displayed on the display device 20. Thus, the field of view display 21*f* may be substantially reproduced on the display device 20, though the patient 14 may not be displayed, but only the acquired images, such as the sinus 134', and the images that are acquired in real time, such as with the endoscope 137. The display device 20, it is understood, may be mobile and positioned for a best view of the user 12.

Whether displayed on the display 20 and/or in the field of view 21*f* with the AV 21, the display of the graphical representations (e.g. the sinus 134' and the instrument 110') may be from the point of view of the user 12. Thus, as the user 12 moves relative to the subject 12, the display in the field of view 21*f* and/or on the display device 20 may alter to provide a display for the user 12 as if the user 12 were looking within the subject 12 at the selected position. In other words, is the user 12 moved to a position at a head of the subject 12 looking inferiorly, rather than superiorly, the display of the graphical representations would be altered to match the position of the user 12 relative to the subject 14. The determined position of the user 12 may be determined, in various embodiments, by the tracker 149 and/or the views of the imaging device 180,182 associated with the AV 21.

Figure 4:
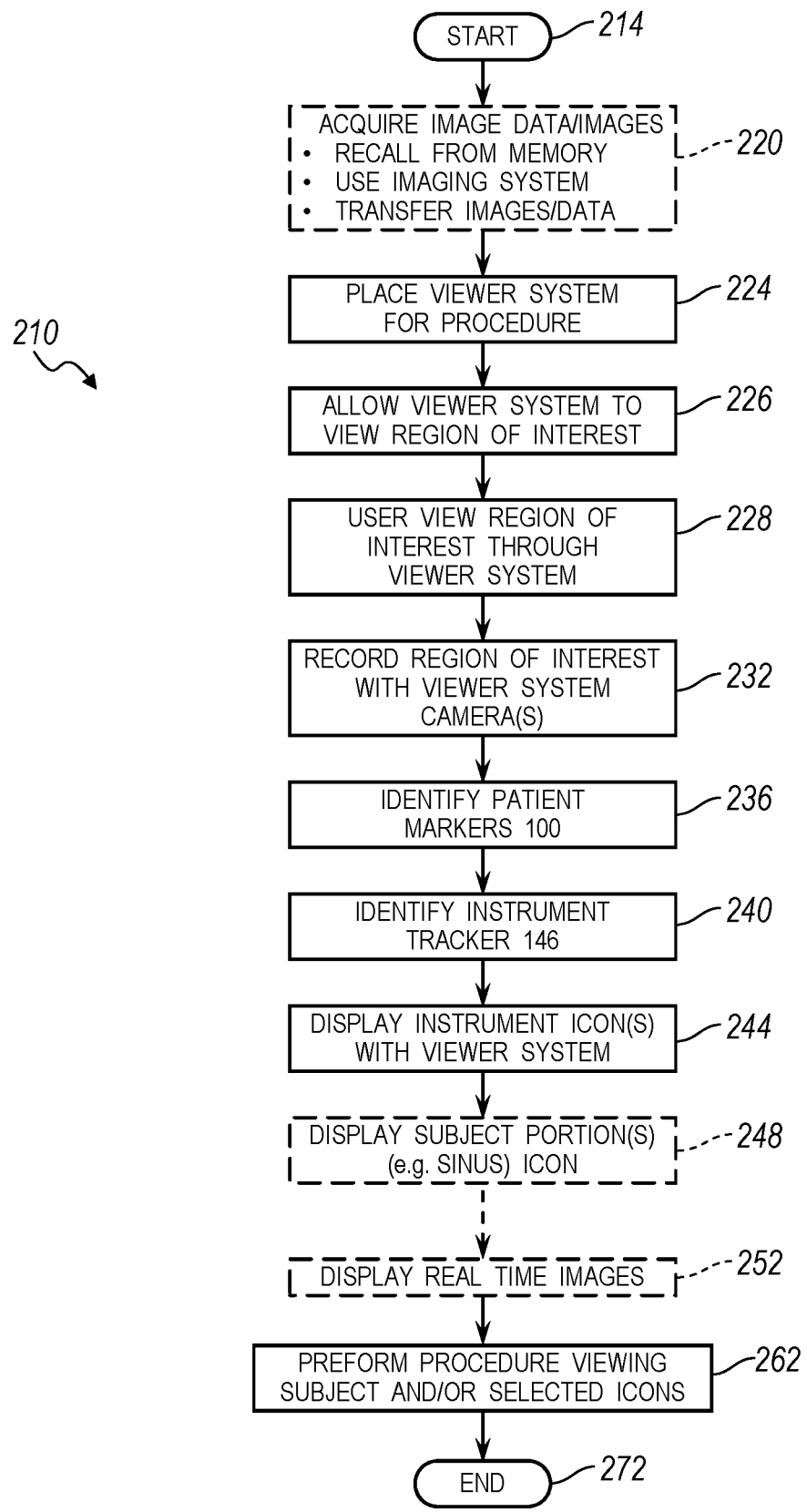
FIG. 4 is a flowchart illustrating an operation of a display system.

With continuing reference to FIGS. 1-3B and additional reference to FIG. 4 a method of using the AV 21 by the user 12 to assist in performing a procedure, such as a procedure relative to one or more of the sinuses including the frontal sinus 136, is described in the flowchart 210. Generally the process may start in the start block 214. After initiating the process in start block 214, acquisition of image data or images of the subject 14 may be performed. Acquisition of the image data or images may be performed in any appropriate manner. For example, images of the subject 14 may be acquired and stored on a memory system, such as the memory system 27 and/or the memory system 33*b*, at a selected time prior to performing a procedure, such as when the patient 14 is prepared for introduction of the instrument 66 into the patient 14. The images may be acquired with a selected imaging system such a CT scanner and/or an MRI and saved in an appropriate format, such as raw data and/or reconstructed images. The reconstructed images may include images that have been rendered in a three-dimensional manner for viewing by the user 12 with varying display devices, such as the display device 20 and/or the AV 21. Further, various portions of the image or image data may be segmented, such as segmenting the sinuses, including the frontal sinus 136 from the other image data. Moreover, the identification of the markers 100 in the image or image data may be performed such as by a processor, including the processor 26 and/or 33*a*. Segmenting the various portions of the anatomy, such as the frontal sinus 136, and/or identifying the markers 100 may be performed using various segmentation techniques. Segmentation techniques may include those incorporated in various imaging and navigation systems such as the FUSION™ navigation system sold by Medtronic, Inc.

Image data may also be acquired substantially during or immediately prior to a procedure such as with the imaging device 14 that may be used substantially intraoperatively (e.g. when the patient is prepared for the procedure). The various portions of the image or image data may be segmented, as discussed above but rather than being stored on the memory prior to the procedure for a selected period of time, the data may be transferred substantially in real time to the processor system 22 for use during the procedure. Nevertheless, it may be understood that the image data may be stored for a selected period of time, such as to analyze and/or process the image data or images for use during the procedure.

The acquisition of the image data may be optional, as preparing images for display by the AV 21 and/or use during a procedure is not required. For example, as discussed herein, the system including the AV 21 and the processor system 22 may track the markers 100 and the tracking device 146 to represent the positon of the instrument without image data of the patient 14. In various embodiments, the images may be accessed by the processor system 22 for display with the AV 21, as discussed above.

The AV 21 may be placed for the procedure in block 224. Placement of the AV 21 for the procedure may include placing the AV 21 on the user 12, as discussed further herein. Moreover, the AV 21 may be placed in communication with the processor system 22 such as for providing processing ability to track the patient 14, such as with the markers 100, and/or the instrument 66, such as with the tracking device 146. The AV 21 may therefore view the region of interest in block 226 and the user may confirm being able to view the region of interest in block 228. In viewing the region of interest, the cameras 180, 182 may be able to view at least the portion of the patient 14 on which a procedure is to occur, such as generally the head region. As discussed above, the region of operation may be substantially unviewable by the user 12 through various external tissues of the patient 14. Therefore, the region of the operation may include the sinuses, such as the frontal sinus 136, and the region of interest may include the entire head of the patient 14. Accordingly, the cameras 180, 182 may be positioned to view the region of interest and the user 12 may confirm viewing the region of interest through the viewscreens 160, 162. The viewscreens 160, 162 are substantially transparent when no icons are displayed on a portion of the viewscreens 160, 162.

Once the AV 21 has the view of the region of interest, a recording of the region of interest with the AV 21 cameras may be performed in block 232. Recording of the region of interest in block 232 may allow for collection of images with the cameras 180, 182 (although it is understood that more than two or less than two cameras may be used). The recording of the region of interest may include imaging at least a portion of the patient 14 in an ongoing manner, such as during the entire procedure. Imaging the region of interest of the patient 14 may include imaging the markers 100 and/or other fiducial points or portions of the patient 14. Accordingly, the recorded region of interest may include identifying patient markers in block 236.

Identifying of patient markers may include segmenting image data recorded at the region of interest in block 232 to identify the patient markers 100 in the image. The identified patient markers 100 may be displayed as an icon with the viewscreens 160, 162 such as with an icon 100*a*' which may include a three-dimensional cube positioned over the marker 100*a* on the patient 14 when viewed by the user 12, as illustrated in FIG. 3. Nevertheless, identifying the patient markers in block 236 may not require or provide for the display of the icon 100*a*' but may simply be performed to identify the marker to identify the region of the patient 14 by the processor system 22 such as for identification of a location of the instrument 66, or a portion thereof, such as the distal end 110, as discussed further herein.

Identifying the markers 100 on the patient 14 allows the processor system, such a portion of the navigation system, to track the patient 14 when the markers 100 are within the field of view of the cameras of the AV 21. The markers 100 may include portions that are identifiable in the image acquired with the cameras 180, 182 such as a color, pattern, shape, etc. Further, the markers 100 may include features that are identifiable for determining a position, including a pose, location and orientation of the marker relative to the AV 21. Therefore, the patient 14 may be tracked relative to the AV 21 worn by the user 12.

In block 240 the instrument tracker 146 may be identified. The instrument tracker 146 may include portions that are identifiable in the image acquired with the cameras 180, 182 such as a color, pattern, shape, etc. Further, the instrument tracker 146 may include features that are identifiable for determining a position, including a pose, location and orientation of the marker relative to the AV 21. For example, the tracking device 146 may include a pattern that is viewable by the cameras 180, 182. The pattern on the tracking device 146 may be substantially or entirely unique from different perspectives relative to the tracking device. Thus, the viewed pattern on the tracking device 146 may be used to determine the positon of the instrument tracker 146 and, therefore, the instrument 66.

The instrument tracker 146 may be fixed to the instrument 66, as discussed above. A geometric relationship between various portions of the instrument 66, such as the distal tip 110 and/or an operating portion 122, may be predetermined and entered for processing by the processor system 22. In various embodiments, the geometry may be saved in the memory 27 and recalled due to automatic identification of the instrument 66 (e.g. by viewing the instrument with the cameras 180, 182) and/or entering the identification of the instrument by the user 12. Nevertheless the AV 21 may be used to view the tracking device 146 to determine a position including a location (e.g. a three-dimensional coordinates) and an orientation in various degrees of freedom (e.g. three-degrees of freedom). The tracked position of the instrument 66 may be used by the processing system 22 for various purposes.

For example, as illustrated in FIG. 3, performed in block 244 the instrument icon 66' may be displayed with the AV 21, such as being displayed on one or more of the viewscreens 160, 162. The viewscreens 160, 162 may be substantially transparent save for the portions illustrating the icons. The icon 66' and/or portions of the instrument such as the distal tip icon 110' and/or the operating portion 122' may be illustrated on the viewscreens 160, 162 relative to the patient 14. The user 12 may then view the patient 14 and the icon or icons through the viewscreens 160, 162. Accordingly the user 12 may view a position of at least a portion of the instrument 66 relative to the patient 14, including a portion of the patient 14.

A display of a subject portion icon may selectively or alternatively be displayed in block 248. For example, as illustrated in FIG. 3A and/or FIG. 3B, the frontal sinus 136' icon may be displayed. The frontal sinus icon 136' may be displayed relative to the instrument icon 66' and the patient 14. Therefore, the user 12 may view the patient 14, the instrument icon 66', and the frontal sinus icon 136'. Due to the tracking of the markers 100 on the patient 14 the relative position of the instrument 66 may be displayed on the viewscreens 160, 162 with the instrument icon 66'. Further the relative position of the subject portion, such as the frontal sinus 136, may be displayed due to registration of the pre-acquired image to the patient using the markers 100, as discussed above.

Again, as the AV 21 is able to track the patient 14 due to the markers 100 the relative positions of the instrument 66 and the subject portions, such as the frontal sinus 136, may be updated in substantially real time and displayed on the viewscreens 160, 162 for viewing by the user 12 along with the subject 14. It is understood that the icons, such as the instrument icon 66' and the subject portion icon 136' may be generated and displayed on the viewscreens 160, 162 while the user is able to view the patient 14 through the viewscreens 160, 162 in real time and in physical space. It is further understood that the icons may be displayed on only or both of the viewscreens 160, 162, as selected by the user 12.

As discussed above, the user 12 may also select to have displayed real time images, optionally, in block 252. The real time images may be images acquired with the endoscope 137, as discussed above and as generally understood by one skilled in the art. The real time images may include surfaces, such as internal surfaces, of the subject 14. Further, or in addition thereto, the images may include displays or images of the instrument 66, such as the distal end 110" display of the instrument 66. The user 12 may select to have the auxiliary image 153 displayed in the field of view 21f or on any appropriate display, such as the display device 20. The user 12 may also select to have the auxiliary display 153 turned off or not displayed such that the user 12 only use the subject 14 and selected augmented reality portions, such as the graphical representation or icons as discussed above. It is further understood, that the user 12 may select to have graphical representations displayed in the auxiliary display area 153 and the real time images displayed superimposed or displayed relative to the subject 14 in the field of view 21f. As discussed above, the images acquired with the endoscope 137 may be registered relative to the subject 14 due to the selected fiducial portions and/or markers on the subject and the patient or subject tracker 64. Thus, the user 12 may view the icons relative to the instrument 66, icons relative to selected sinuses or internal portions in part or because of the pre-acquired images (e.g. MRI and/or CT image), and real time images acquired with the endoscope 137 or other appropriate imaging system.

In block 262 a procedure may be performed by viewing the subject 14 and selected icons, such as the instrument icon 66' and/or the frontal sinus icon 136' due to the AV 21. It is further understood that other appropriate icons may be displayed such as the maxillary sinus icon 134' and/or the sphenoid sinus icon 138'. Moreover, additional instrument icons may also be displayed due to various tracking devices associated with instruments. Further different instruments maybe have different geometries that may also be entered and/or recalled prior to displaying an icon on the display device, including the AV 21. The method 210 may then end in block 272 including various other procedures, such as various staunching and/or closing procedures.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for viewing a subject when performing an operation on the subject, comprising:
    a user wearable viewscreen and camera system configured to be carried by a single user and having a field of view, the viewscreen and camera system including:
        a first viewscreen configured to be positioned near a first eye of a user;
        a second viewscreen configured to be positioned near a second eye of the user; and
        at least a first camera configured to have a first field of view from the user wearable viewscreen and camera system when worn by the single user;
    an instrument tracking device fixable to an instrument that is separate from the user wearable viewscreen and camera system and is viewable by the first camera;
    a subject marker fixed to the subject at a first location on the subject and having an identifiable shape viewable by the first camera;
    a user wearable viewscreen and camera system tracking device fixed to the user wearable viewscreen and camera system configured to allow the user wearable viewscreen and camera system to be tracked and registered relative to the subject;
    a processor system configured to execute instructions (i) to determine a relative position of the instrument tracking device relative to the subject marker fixed to the subject based on a first signal from the first camera and (ii) generate an instrument representation to be displayed in at least one of the first viewscreen or the second viewscreen to be viewed by at least one of the first eye or the second eye; and a supplemental viewing area displayed within the field of view of the single user with the user wearable viewscreen and camera system, where the single user can selectively select or choose information to be displayed in the supplemental viewing area including displaying real time images, pre-acquired images, and other information in the supplemental viewing area;

wherein the processor system is further configured to generate an anatomy representation;

wherein the instrument representation is represented as an instrument icon and the anatomy representation is represented as an anatomy icon;

wherein the instrument icon and the anatomy icon each have a selected opacity to view both the instrument icon and the anatomy icon substantially simultaneously such that the instrument icon can be viewed within the anatomy icon substantially simultaneously;

wherein the first viewscreen or the second viewscreen are substantially transparent and configured to allow the user to view the subject, through the first or second viewscreens;

wherein the processor system is further configured to generate the instrument icon and the anatomy icon and display the instrument icon and anatomy icon at a position spaced away from the subject on at least one of the first view screen or the second view screen to allow the single user to have a substantially unobstructed view of the subject while viewing the instrument icon and the anatomy icon.

2. The system of claim 1, wherein the user wearable viewscreen and camera system further comprises:

a second camera configured to have a second field of view;

wherein the processor system is further operable to execute instructions (i) to determine a relative position of the instrument tracking device relative to the subject marker fixed to the subject based on the first signal from the first camera and a second signal from the second camera regarding a view of the instrument tracking device relative to the subject marker.

3. The system of claim 2, wherein the instrument representation is viewed as a single representation by the user when displayed on both the first viewscreen and the second viewscreen.

4. The system of claim 3, wherein the instrument representation appears to the user as a portion of the instrument in a field of vision of the user including the subject.

5. The system of claim 3, further comprising:

a memory having stored thereon an image of at least a portion of a region of operation of the subject;

wherein the image includes image portions that represent the subject marker fixed to the subject at the first location;

wherein the processor system executes further instructions to (i) register the image of at least the portion of the region of the operation and (ii) display the anatomy representation with at least one of the first viewscreen or the second viewscreen;

wherein the anatomy representation is configured to appear in the user's field of vision relative to the subject.

6. The system of claim 5, wherein the instrument representation and the anatomy representation are both configured to appear in the user's field of vision relative to the subject.

7. The system of claim 1, wherein the first field of view and the second field of view overlap.

8. The system of claim 1, further comprising the instrument moveable relative to the subject and connectable to the instrument tracking device, wherein the instrument tracking device is an annular member with a plurality viewable tracking members on the annular member.

9. A system for viewing a subject when performing an operation on the subject, comprising:

a user wearable viewscreen and camera system configured to be carried by a single user and held relative to a first eye of the single user, having a field of view, the user wearable viewscreen and camera system including:

a mounting structure;

a first viewscreen configured to be positioned near the first eye of the user and fixed to the mounting structure; and a first camera configured to have a first field of view from the user wearable viewscreen and camera system when worn by the single user;

an instrument tracking device fixed to an instrument viewable by the first camera;

a subject marker fixed to the subject at a first location on the subject and having an identifiable shape viewable by the first camera;

a user wearable viewscreen and camera system tracking device fixed to the user wearable viewscreen and camera system configured to allow the user wearable viewscreen and camera system to be tracked and registered relative to the subject;

a processor system configured to execute instructions (i) to determine a relative position of the instrument tracking device relative to the subject marker fixed to the subject based on a first signal from the first camera regarding a view of the instrument tracking device relative to the subject marker and (ii) generate an instrument icon to be displayed in the first viewscreen to be viewed by the first eye; and a supplemental viewing area displayed within the field of view of the user wearable viewscreen and camera system, where the single user can selectively select or choose information to be displayed in the supplemental viewing area including displaying real time images, pre-acquired images, and other information in the supplemental viewing area;

wherein the instrument representation is represented as the instrument icon and an anatomy representation is represented as an anatomy icon;

wherein the instrument icon and the anatomy icon each have a selected opacity to view both the instrument icon and the anatomy icon substantially simultaneously such that the instrument icon can be viewed within the anatomy icon substantially simultaneously;

wherein the first viewscreen is substantially transparent and configured to allow the user to view the subject, through the viewscreen;

wherein the processor system is further configured to generate the instrument icon and the anatomy icon and display the instrument icon and anatomy icon at a position spaced away from the subject on the first view screen to allow the single user to have a substantially unobstructed view of the subject while viewing the instrument icon and the anatomy icon.

10. The system of claim 9, wherein the wearable viewscreen and camera further include:

a second camera configured to have a second field of view and fixed to the mounting structure;

wherein the first field of view is different than the second field of view;
wherein the first camera is fixed to the mounting structure; and
a second viewscreen configured to be positioned near a second eye of the user.

11. The system of claim 10, wherein the wearable viewscreen and camera is configured so that the user is able to simultaneously view the subject through both of the first viewscreen and the second viewscreen.

12. The system of claim 10, wherein the wearable viewscreen and camera is configured so that the user is able to simultaneously view both the subject and the instrument icon.

13. The system of claim 12, wherein the processor system configured to execute further instructions to register (i) pre-acquired images of the subject wherein the pre-acquired image includes an image of the subject marker fixed to the subject at the first location with (ii) a view of the subject with the first camera and the second camera;
wherein at least a portion of pre-acquired image is displayed with at least one of the first viewscreen or the second viewscreen registered to the subject;
wherein the instrument icon is illustrated at a determined position of the instrument relative to at least the portion of pre-acquired image with at least one of the first viewscreen or the second viewscreen.

14. A method for viewing a subject when performing an operation on the subject, comprising:
providing a user wearable viewscreen and camera system configured to be carried by a single user including:
(i) a first viewscreen configured to be positioned near a first eye of the single user;
(ii) a second viewscreen configured to be positioned near a second eye of the single user;
(iii) at least a first camera configured to have a first field of view or a second camera configured to have a second field of view relative to the first viewscreen and the second viewscreen from the user wearable single viewscreen and camera system when worn by the single user; and
(iv) a user wearable viewscreen and camera system tracking device fixed to the user wearable viewscreen and camera system configured to allow the user wearable viewscreen and camera system to be tracked and registered relative to the subject;
placing an instrument tracking device fixed to an instrument in the first field of view of the first camera or the second field of view of the second camera;
fixing a subject marker to the subject at a first location having an identifiable shape to be viewable by at least the first camera or the second camera;
operating a processor system to execute instructions (i) to determine a relative position of the instrument tracking device relative to the subject marker fixed to the subject based on a first signal from the first camera or a second signal from the second camera regarding a view of the instrument tracking device relative to the subject marker and (ii) generate an instrument icon to be displayed in at least one of the first viewscreen or the second viewscreen to be viewed by at least one of the first eye or the second eye; and
displaying a supplemental viewing area within the first or second field of view, where the single user can selectively select or choose information to be displayed in the supplemental viewing area including displaying real time images, pre-acquired images, and other information in the supplemental view area;
wherein the instrument representation is represented as the instrument icon and an anatomy representation is represented as an anatomy icon;
wherein the instrument icon and the anatomy icon each have a selected opacity to view both the instrument icon and the anatomy icon substantially simultaneously such that the instrument icon can be viewed within the anatomy icon substantially simultaneously;
wherein the first viewscreen or the second viewscreen are substantially transparent and configured to allow the user to view the subject, through the first or second viewscreens;
wherein the processor system is further configured to generate the instrument icon and the anatomy icon and display the instrument icon and anatomy icon at a position spaced away from the subject on at least one of the first view screen or the second view screen to allow the single user to have a substantially unobstructed view of the subject while viewing the instrument icon and the anatomy icon.

15. The method of claim 14, further comprising:
providing the instrument to have an operating end configured to be positioned in a region of operation for performing the operation on the subject.

16. The method of claim 15, further comprising:
operating the processor system to execute instructions to recall from a memory system a position of the operating end relative to the instrument tracking device.

17. The method of claim 16, further comprising:
configuring at least one of the first viewscreen or the second viewscreen for the single user to simultaneously view the subject and the instrument icon.

18. The method of claim 17, further comprising:
configuring the instrument to move relative to the subject while the single user is able to simultaneously view the subject and the instrument icon.

19. The method of claim 18, further comprising:
performing a procedure while simultaneously viewing the subject and the instrument icon.

* * * * *

UNITED STATES PATENT AND TRADEMARK OFFICE
CERTIFICATE OF CORRECTION

| | | |
|---|---|---|
| PATENT NO. | : 11,944,272 B2 | Page 1 of 1 |
| APPLICATION NO. | : 16/210647 | |
| DATED | : April 2, 2024 | |
| INVENTOR(S) | : Kyle A. Godwin et al. | |

It is certified that error appears in the above-identified patent and that said Letters Patent is hereby corrected as shown below:

In the Specification

Column 3, Detailed Description, Line 31, Delete "141." and insert --14L.-- therefor Column 3, Detailed Description, Line 44, Delete "18," and insert --20,-- therefor Column 3, Detailed Description, Line 47, Delete "21" and insert --20-- therefor Column 6, Detailed Description, Line 9, Delete "26" and insert --22-- therefor Column 9, Detailed Description, Line 49, Delete "14" and insert --16-- therefor Column 10, Detailed Description, Line 19, Delete "18" and insert --16-- therefor Column 14, Detailed Description, Line 42, Delete "subject 12," and insert --subject 14,-- therefor Column 14, Detailed Description, Line 45, Delete "subject 12" and insert --subject 14-- therefor Column 14, Detailed Description, Line 47, Delete "subject 12" and insert --subject 14-- therefor Column 14, Detailed Description, Line 52, Delete "180,182" and insert --16-- therefor Column 15, Detailed Description, Line 21, Delete "14" and insert --16-- therefor Column 15, Detailed Description, Line 37, Delete "positon" and insert --position-- therefor Column 16, Detailed Description, Line 48, Delete "positon" and insert --position-- therefor Column 17, Detailed Description, Lines 14-15, Delete "136' icon" and insert --icon 136'-- therefor Signed and Sealed this
Thirtieth Day of September, 2025

John A. Squires
*Director of the United States Patent and Trademark Office*